United States Patent [19]

Tomikawa et al.

[11] Patent Number: 5,141,751
[45] Date of Patent: Aug. 25, 1992

[54] LIPID MEMBRANE STRUCTURES

[75] Inventors: Munehiro Tomikawa; Sadao Hirota; Hitoshi Yamauchi; Hiroshi Kikuchi; Yasuyoshi Kawato, all of Tokyo, Japan

[73] Assignee: Daiichi Pharmaceutical Co., Ltd., Tokyo, Japan

[21] Appl. No.: 663,775

[22] Filed: Mar. 4, 1991

Related U.S. Application Data

[63] Continuation of Ser. No. 373,838, Jun. 29, 1989, abandoned.

[30] Foreign Application Priority Data

Jun. 29, 1988 [JP] Japan .................. 63-162153

[51] Int. Cl.$^5$ .............................................. A61K 9/127
[52] U.S. Cl. ...................... 424/450; 264/4.1; 264/4.3; 264/4.6; 428/402.2; 514/2; 436/829
[58] Field of Search ............... 424/450, 1.1; 260/403, 260/410; 264/4.1, 4.3, 4.6; 428/402.2, 430; 514/2; 436/829

[56] References Cited

U.S. PATENT DOCUMENTS

| | | | |
|---|---|---|---|
| 4,744,989 | 5/1988 | Payne et al. | 424/493 |
| 4,804,539 | 2/1989 | Guo et al. | 436/829 X |
| 4,830,858 | 5/1989 | Payne et al. | 424/450 |
| 4,874,553 | 10/1989 | Hager et al. | 260/403 |
| 4,892,733 | 1/1990 | Bichon et al. | 424/450 X |
| 4,897,308 | 1/1990 | Vanlerberghe et al. | 424/450 X |
| 4,917,951 | 4/1990 | Wallach | 424/450 X |
| 4,983,397 | 1/1991 | Schroit et al. | 424/450 |
| 5,021,200 | 6/1991 | Vanlerberghe et al. | 424/450 X |

FOREIGN PATENT DOCUMENTS 3621306  1/1987  Netherlands .
WOA387049-26  5/1988  PCT Int'l Appl. .

Primary Examiner—Thurman K. Page
Assistant Examiner—Neil Levy
Attorney, Agent, or Firm—Sughrue, Mion, Zinn, Macpeak & Seas

[57] ABSTRACT

Lipid membrane structures containing, in the lipid membrane thereof, a compound represented by formula (I):

$$R_3-(CH_2)_n\overset{\overset{\displaystyle NHR_1}{|}}{C}HCOOR_2 \qquad (I)$$

wherein $R_1$ represents a hydrogen atom or a fatty acid residue; $R_2$ represents a hydrogen atom or an acyclic hydrocarbon residue; $R_3$ represents an amino group, a guanidino group or an amidino group; and n represents an integer of from 1 to 6; provided that $R_1$ and $R_2$ do not represent hydrogen atoms at the same time, or a salt thereof. The lipid membrane structures exhibit excellent specific affinity for tumor cells and can be delivered preferentially to tumor cells.

6 Claims, No Drawings

LIPID MEMBRANE STRUCTURES

This is a continuation of application Ser. No. 07/373,838 filed Jun. 29, 1989, now abandoned.

FIELD OF THE INVENTION

This invention relates to lipid membrane structures which are delivered preferentially to tumor cells, etc., and are therefore useful as a drug carrier in medical treatment.

BACKGROUND OF THE INVENTION

In the studies of liposomes which are delivered preferentially to tumor cells, methods for modifying liposomal surfaces with monoclonal antibodies have hitherto been reported, e.g., in Tadakuma, *Iyaku Journal*, Vol. 20, p. 643 (1984), Tadakuma, *Saibo Kogaku*, Vol. 1, p. 72 (1982), Ohsawa et al., *Chemical and Pharmaceutical Bulletin*, Vol. 35, p. 740 (1987), and Papahadjopoulos et al., *Cancer Research*, Vol. 46, p. 4,904 (1986). In particular, Ohsawa et al. reported that small unilamellar liposomes modified with anti-carcinoembryonic antigen antibodies were easily taken up by tumor cells to exhibit enhanced antitumor effects.

Under the present situation, however, the monoclonal antibodies are difficult to commercialize because of the difficulty of mass-production.

SUMMARY OF THE INVENTION

One object of this invention is to provide lipid membrane structures which are delivered preferentially to tumor cells and can be mass-produced with good reproducibility.

As a result of extensive investigations, the inventors have found that the above object of this invention can be accomplished by lipid membrane structures containing, in the lipid membrane thereof, the compound represented by formula (I):

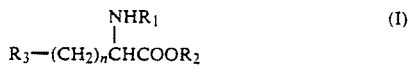

wherein $R_1$ represents a hydrogen atom or a fatty acid residue; $R_2$ represents a hydrogen atom or an acyclic hydrocarbon residue; $R_3$ represents an amino group, a guanidino group or an amidino group; and n represents an integer of from 1 to 6; provided that $R_1$ and $R_2$ do not represent hydrogen atoms at the same time, or a salt thereof.

DETAILED DESCRIPTION OF THE INVENTION

In formula (I), the term "fatty acid residue" means a group derived from a saturated or unsaturated fatty acid which may have a branch by removing one hydroxyl group therefrom. Specific examples of the fatty acid residue include those having from 1 to 30 carbon atoms, preferably from 14 to 20 carbon atoms, e.g., formyl, acetyl, propanoyl, butanoyl, pentanoyl, hexanoyl, heptanoyl, octanoyl, decanoyl, dodecanoyl, tridecanoyl, tetradecanoyl, pentadecanoyl, hexadecanoyl, heptadecanoyl, octadecanoyl, nonadecanoyl, eicosanoyl, heneicosanoyl, docosanoyl, tricosanoyl, tetracosanoyl, hexacosanoyl, triacontanoyl, 9-hexadecenoyl, 9-octadecenoyl, 9,12-octadecadienoyl, 9,12,15-octadecatrienoyl, 11-eicosenoyl, 11,14-eicosadienoyl, 11,14,17-eicosatrienoyl, 4,8,12,16-eicosatetraenoyl, 13-docosenoyl, 4,8,12,15,19-docosapentaenoyl, 15-tetracosenoyl, 2-dodecylhexadecanoyl, 2-tetradecylhexadecanoyl, 2-dodecyltetradecanoyl, 2-tetradecenylhexadecenoyl, 2-tetradecylhexadecenoyl, 2-tetradecenylhexadecanoyl and 2-dodecyloctadecanoyl groups.

The term "acyclic hydrocarbon residue" means a group derived from a saturated or unsaturated acyclic hydrocarbon which may have a branch by removing one hydrogen atom therefrom. Specific examples of the acyclic hydrocarbon residue include those having from 1 to 30 carbon atoms, preferably from 14 to 20 carbon atoms, e.g., methyl, ethyl, propyl, butyl, pentyl, hexyl, heptyl, octyl, nonyl, decyl, dodecyl, tridecyl, tetradecyl, pentadecyl, hexadecyl, heptadecyl, octadecyl, nonadecyl, eicosyl, heneicosyl, docosyl, tricosyl, tetracosyl, hexacosyl, triacontyl, 9-hexadecenyl, 9-octadecenyl, 9,12-octadecadienyl, 9,12,15-octadecatrienyl, 11-eicosenyl, 11,14-eicosadienyl, 11,14,17-eicosatrienyl, 4,8,12,16-eicosatetraenyl, 13-docosenyl, 4,8,12,15,19-docosapentaenyl, 15-tetracosenyl, 2-dodecyltetradecyl, 2-dodecylhexadecyl, 2-tetradecylhexadecyl, 2-tetradecylhexadecenyl, 2-tetradecenylhexadecyl, and 2-dodecyloctadecyl groups.

"n" in formula (I) preferably represents 3 or 4.

Of the compounds represented by formula (I), preferred are those wherein $R_1$ is a fatty acid residue and $R_2$ is an acyclic hydrocarbon residue. In these preferred compounds, the total number of the carbon atoms of $R_1$ and $R_2$ is preferably in the range of from 10 to 40.

The "lipid membrane structures" according to the present invention means lamellar lipid particles wherein polar head groups of a polar lipid are arranged to face an aqueous phase of an interface to form membrane structures. Examples of the lipid membrane structures include liposomes, micelles, microemulsions, and the like.

A process for preparing the lipid membrane structures containing the compound of formula (I) or a salt thereof in the lipid membrane thereof is described below.

(a) Preparation of Liposomes Containing Compound (I) or Salt Thereof in Liposomal Membrane An aqueous dispersion of liposomes is prepared from membrane components, such as phospholipids (e.g., phosphatidylcholine, phosphatidylglycerol, sphingomyelin, and phosphatidylethanolamine), glycolipids, and dialkyl-type synthetic surfactants according to the known methods as disclosed, e.g., in *Annual Review of Biophysics and Bioengineering*, Vol. 9, p. 467 (1980). The liposomes may further contain sterols (e.g., cholesterol and cholestanol), dialkylphosphates, diacylphosphatidic acids, stearylamine, α-tocopherol, etc., in the liposomal membrane.

To the liposomal dispersion thus prepared is added an aqueous solution of the compound of formula (I) or a salt thereof, and the mixture is allowed to stand for a given period of time, preferably under warming at a temperature more than the phase transition temperature of the membrane or above 40° C, followed by cooling to thereby prepare liposomes containing the compound of formula (I) or a salt thereof in the liposomal membrane. Alternatively, the desired liposomes can also be prepared by previously mixing the above-described membrane components and the compound of formula (I) or a salt thereof, and treating the mixture in accordance with the known methods for preparing liposomes.

(b) Preparation of Micelles Containing Compound (I) or Salt Thereof in Micellar Membrane A micelle-forming surfactant, such as polyoxyethylene sorbitan fatty acid esters, polyoxyethylene castor oil derivatives, polyoxyethylene hardened castor oil derivatives, fatty acid sodium salts, sodium cholates, polyoxyethylene fatty acid esters, and polyoxyethylene alkyl ethers, alkyl glycosides, is added to water at a concentration above the critical micelle concentration to prepare a micellar dispersion. To the micellar dispersion is added an aqueous solution of the compound of formula (I) or a salt thereof, and the mixture is allowed to stand for a given period of time, preferably under warming at 40° C. or higher, followed by cooling to thereby prepare micelles containing the compound of formula (I) or a salt thereof in the micellar membrane. Alternatively, the desired micelles can also be prepared by previously mixing the above-described micelle-forming substances and the compound of formula (I) or a salt thereof and treating the mixture according to the known methods for micelles formation.

(c) Preparation of Microemulsions Containing Compound (I) or Salt Thereof in Lipid Membrane Thereof To the micelles as prepared in (b) above are added fats and oils, such as soybean oil, to saturate the micelles with the fats and oils, and to increase the oily phase to such a degree that no irreversible oil phase separation may not occur, to thereby prepare microemulsions containing the compound of formula (I) or a salt thereof in the lipid membrane thereof. Alternatively, the desired microemulsions can also be prepared by adding an aqueous solution of the compound of formula (I) or a salt thereof to microemulsions previously prepared according to known methods, and the resulting emulsions are allowed to stand for a given period of time, preferably under warming at 40° C. or higher, followed by cooling.

In some cases of the above-described processes, the form of the resulting lipid membrane structures may be varied by controlling the proportion of the compound of formula (I) or a salt thereof to the total content of the lipid components. For instance, in the case that phosphatidylcholine is used as a sole lipid component, liposomes can be produced when a molar ratio of the compound of formula (I) or a salt thereof to the total content of the lipid components is adjusted to about ⅔ or less; and micelles or microemulsions can be produced when the above-described molar ratio is greater than ⅔.

In order to deliver preferentially the lipid membrane structures according to the present invention to tumor cells, etc., it is usually desirable to use the compound of formula (I) or a salt thereof at a molar ratio of at least about 1/40 to the total content of the lipid components.

The compound of formula (I) can be prepared by known methods, and typical processes for preparing the compound of formula (I) are illustrated below.

(1) Preparation of Compound (I) [$R_3$: guanidino group]

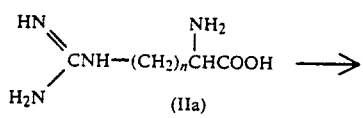

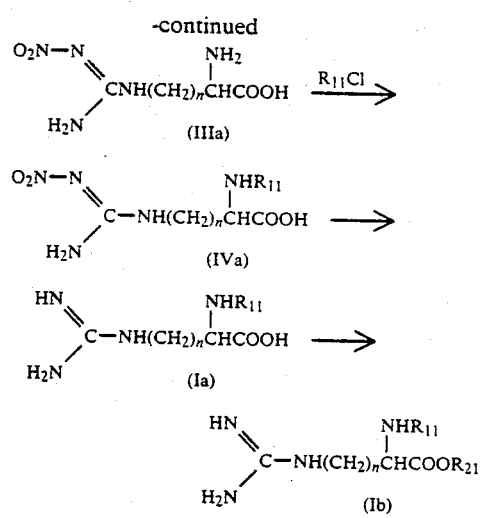

wherein $R_{11}$ represents a fatty acid residue; $R_{21}$ represents an acyclic hydrocarbon residue; and n is as defined above.

The compound of formula (IIa) can be reacted with nitric acid in an appropriate organic solvent in the presence of sulfuric acid to prepare the compound of formula (IIIa). The compound of formula (IIIa) can be reacted with a fatty acid chloride ($R_{11}Cl$) in an appropriate organic solvent in the presence of a base, e.g., sodium hydroxide, to prepare the compound of formula (IVa), which can be then catalytically reduced in an appropriate organic solvent in the presence of a catalyst, e.g., palladium carbon, to prepare the desired compound of formula (Ia). The compound of formula (Ib) can then be obtained by esterification of the compound of formula (Ia) with a compound of formula $R_{21}OH$ in an appropriate organic solvent in the presence of an acid.

When the compound of formula (IIa) is reacted according to the esterification, a compound of formula (I) wherein $R_1$ is a hydrogen atom, $R_2$ is an acyclic hydrocarbon residue, and $R_3$ is a guanidino group can be obtained.

(2) Preparation of Compound (I) [$R_3$: amino group]

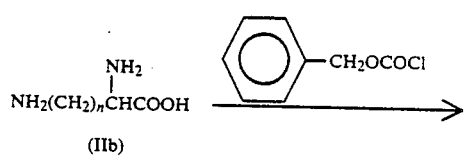

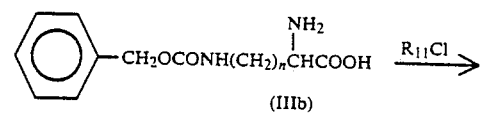

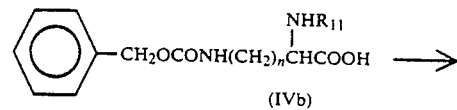

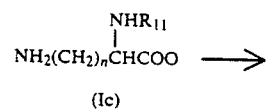

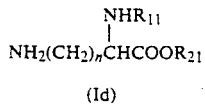

wherein $R_{11}$, $R_{21}$, and n are as defined above.

The compound of formula (IIb) can be reacted with benzyloxycarbonyl chloride in an appropriate organic solvent to prepare the compound of formula (IIIb). The compound of formula (IIIb) can be reacted with a fatty acid chloride $R_{11}Cl$ in an appropriate organic solvent in the presence of an alkali, e.g., sodium hydroxide, to prepare the compound of formula (IVb). The compound of formula (IVb) can be catalytically reduced in an appropriate organic solvent in the presence of a catalyst, e.g., palladium carbon, to prepare the compound of formula (Ic). The compound of formula (Ic) can be then esterified with a compound of formula $R_{21}OH$ in an appropriate organic solvent in the presence of an acid to obtain the compound of formula (Id).

When the compound of formula (IIb) is reacted according to the esterification, a compound of formula (I) wherein $R_1$ is a hydrogen atom, $R_2$ is an acyclic hydrocarbon residue, and $R_3$ is an amino group can be produced.

The compound of formula (I) has optical isomers. These isomers and a mixture thereof are included in the scope of the present invention.

Drugs that may be encapsulated in the lipid membrane structures of the present invention vary depending on the type of the membrane structures. For example, the drugs that may be encapsulated in the liposomes are not particularly limited and include water-soluble drugs and lipid soluble drugs, such as Methotrexate and Cisplatin. The drugs which may be encapsulated in the micelles or microemulsions include lipid soluble drugs.

In the lipid membrane of the present invention, the compound of formula (I) or a salt thereof is firmly incorporated into the lamellar lipid membrane thereof through a hydrophobic interaction. It has been confirmed by gel filtration and Test Example 1 hereinafter given that the proportion of the compound of formula (I) or a salt thereof that exists as a free monomer to that in the lipid membrane is very low.

The lipid membrane structures according to the present invention possess excellent specific affinity for tumor cells, therefore, the lipid membrane structures of the present invention can be delivered preferentially to tumor cells. Further, the compound of formula (I) and salts thereof can be produced chemically on a large scale, therefore, the lipid membrane structures of the present invention can be prepared in large quantity with good reproducibility.

The present invention is now illustrated in greater detail by way of the following Examples and Test Examples, but it should be understood that the present invention is not deemed to be limited thereto.

COMPARATIVE EXAMPLE 1

Dipalmitoylphosphatidylcholine (hereinafter abbreviated as DPPC) and cholesterol were put in a test tube at a molar ratio of 1:1 to a total lipid amount of 8 μmol and dissolved in chloroform. The chloroform was then removed in a nitrogen gas stream to form a lipid film on the inner wall of the tube. Two milliliters of a phosphate-buffered saline (pH=7.4, hereinafter abbreviated as PBS) were added thereto. After shaking in a vortex mixer, the mixture was subjected to sonication to prepare a liposomal dispersion. The dispersion was warmed to 45° to 50° C. and then passed through a polycarbonate membrane filter having a pore size of 0.2 μm to prepare a liposomal dispersion having a particle size of not greater than 0.2 μm. The dispersion was subjected to ultracentrifugation (150,000×g, 1 hour, twice), the supernatant was removed, and 5 ml of PBS was added to obtain a liposomal dispersion.

EXAMPLE 1

DPPC, cholesterol, and $N^\alpha$-cocoyl-L-arginine ethyl ester (hereinafter abbreviated as CAEE) were put in a test tube at a molar ratio of 1:1:0.05 to a total lipid amount of 8 μmol and dissolved in a 9:1 (by volume) mixture of chloroform and methanol. The solution was then treated in a similar manner to that in Comparative Example 1 to prepare a liposomal dispersion.

EXAMPLE 2

DPPC, cholesterol, and CAEE were put in a test tube at a molar ratio of 1:1:0.1 to a total lipid amount of 8 μmol and then the solution was treated in a similar manner to that in Comparative Example 1 to prepare a liposomal dispersion.

EXAMPLE 3

DPPC, cholesterol, and CAEE were put in a test tube at a molar ratio of 1:1:0.15 to a total lipid amount of 8 μmol and dissolved in a 9:1 (by volume) mixture of chloroform and methanol. The solution was then treated in a similar manner to that in Comparative Example 1 to prepare a liposomal dispersion.

EXAMPLE 4

DPPC, cholesterol, and $N^\alpha$-palmitoyl-L-arginine (hereinafter abbreviated as PAA) were placed in a test tube at a molar ratio of 1:1:0.05 to a total lipid amount of 8 μmol and dissolved in a 9:1 (by volume) mixture of chloroform and methanol. The solution was then treated in a similar manner to that in Comparative Example 1 to prepare a liposomal dispersion.

EXAMPLE 5

DPPC, cholesterol, and PAA were placed in a test tube at a molar ratio of 1:1:0.1 to a total lipid amount of 8 μmol and dissolved in a 9:1 (by volume) mixture of chloroform and methanol. The solution was then treated in a similar manner to that in Comparative Example 1 to prepare a liposomal dispersion.

EXAMPLE 6

DPPC, cholesterol, and PAA were put in a test tube at a molar ratio of 1:1:0.15 to a total lipid amount of 8 μmol and dissolved in a 9:1 (by volume) mixture of chloroform and methanol. The solution was then treated in a similar manner to that in Comparative Example 1 to prepare a liposomal dispersion.

COMPARATIVE EXAMPLE 2

In a test tube, 5.54 μmol of egg yolk lecithin, 1.85 μmol of cholesterol, and 0.62 μmol of phosphatidic acid were dissolved in a 9:1 (by volume) mixture of chloroform and methanol, and 4.0 μCi of $^3H$-dipalmitoylphosphatidylcholine was added to the solution. The organic solvent was then removed from the solution in a nitrogen gas stream to form a lipid film on the inner wall of the test tube. To the tube was added 5 ml of PBS, and the mixture was shaken in a vortex mixer and then subjected to sonication to obtain a liposomal dispersion. The dispersion was warmed to 40° to 45° C. and passed through a polycarbonate membrane filter having a pore size of 0.2 μm to obtain a liposomal dispersion

EXAMPLE 7

In a test tube were put 4.8 μmol of egg yolk phosphatidylcholine, 1.6 μmol of cholesterol, 1.07 μmol of phosphatidic acid, and 0.53 μmol of CAEE. The lipids in the test tube were dissolved in a 9:1 (by volume) mixture of chloroform and methanol, and 2 μCi of $^3$H-dipalmitoylphosphatidylcholine was added thereto. The solution was then treated in a similar manner to that in Comparative Example 2 to prepare a liposomal dispersion.

EXAMPLE 8

A liposomal dispersion was prepared in a similar manner to that in Example 7, except for using 4.24 μmol of egg yolk phosphatidylcholine, 1.41 μmol of cholesterol, 1.41 μmol of phosphatidic acid, and 0.94 μmol of CAEE.

EXAMPLE 9

In a test tube, 4.21 μmol of distearoylphosphatidylcholine, 2.11 μmol of dicetylphosphoric acid, and 1.68 μmol of CAEE were dissolved in a 9:1 (by volume) mixture of chloroform and methanol. The organic solvent was then removed in a nitrogen gas stream to form a lipid film on the inner wall of the test tube. Five milliliters of a PBS solution of 1 mM inulin containing 300 μCi of $^3$H-inulin were added to the test tube, and the mixture was treated in a similar manner to that in Comparative Example 2 to prepare a liposomal dispersion. The resulting liposomal dispersion was subjected to ultracentrifugation (150,000×g, 1 hour, twice), and the supernatant was separated to remove the inulin unencapsulated in the liposomes. PBS was added to the residue to obtain 2.5 ml of a liposomal dispersion encapsulating inulin in the inner aqueous phase thereof.

As a result of enzyme assay using the choline residue of the distearoylphosphatidylcholine as a marker, it was found that the total lipid content of the resulting dispersion was 2.2 μmol per ml. Further, the encapsulation efficiency of inulin in the liposomes was found to be 1.8%.

TEST EXAMPLE 1

A zeta potential of each of the liposomal suspensions prepared in Comparative Example 1 and Examples 1 to 6 was measured with Zetasizer II (trademark; manufactured by Malvern Co., Ltd.). The measurement was conducted by using a capillary type cell having an inner diameter of 0.7 mm under conditions of 25° C. in temperature; 0.8903 poise in solvent viscosity; 1.33 in solvent refractive index; 90 V in cell voltage; and 2 mA in cell current. The results obtained are shown in Table 1 below.

TABLE 1

| ζ Potential of Liposome Suspension | |
|---|---|
| Example No. (Molar Ratio) | ζ Potential (mV) |
| Comparative Example 1 (DPPC:cholesterol = 1:1) | −1.97 |
| Example 1 (DPPC:cholesterol:CAEE = 1:1:0.05) | +2.72 |
| Example 2 (DPPC:cholesterol:CAEE = 1:1:0.1) | +7.81 |

TABLE 1-continued

| ζ Potential of Liposome Suspension | |
|---|---|
| Example No. (Molar Ratio) | ζ Potential (mV) |
| Example 3 (DPPC:cholesterol:CAEE = 1:1:0.15) | +11.2 |
| Example 4 (DPPC:cholesterol:PAA = 1:1:0.05) | −4.20 |
| Example 5 (DPPC:cholesterol:PAA = 1:1:0.1) | −4.54 |
| Example 6 (DPPC:cholesterol:PAA = 1:1:0.15) | −4.93 |

The results of Table 1 revealed that the compound of formula (I) is incorporated into the liposomal membrane.

TEST EXAMPLE 2

1) A suspension culture of MH-134 (murine hepatoma cells) (medium: RPMI-1640; pH=7) was subjected to centrifugation (1,000 rpm, 10 mins.), and the supernatant was removed. PBS was added to the precipitate to resuspend the cells to prepare a cell suspension. Four ml portions of the cell suspension each containing 4×10⁶ cells were put in 18 test tubes and kept at 37° C.

Each of the liposomal dispersions prepared in Comparative Example 2 and Examples 7 and 8 having been previously warmed at 37° C. was added to 6 out of 18 tubes containing the cell suspension in such an amount that the total lipid content became 0.32 μmol. Three out of 6 tubes per sample were incubated for 1 hour, and the other three tubes per sample for 3.5 hours, at 37° C. without shaking. The each mixture was centrifuged (1,000 rpm, 10 mins., twice in PBS) to collect the cells only. The uptake of the lipid by tumor cells was determined by measuring the radioactivity according to a liquid scintillation method. The results obtained were shown in Table 2. The numbers of cells after the incubation were corrected by quantitative determination of protein by Lowry's method.

2) Testing was carried out in the same manner as in 1) above, except that the PBS used for re-suspending tumor cells contained 5% of fetal bovine serum. The results obtained are shown in Table 3.

3) Testing was carried out in the same manner as in 1) above, except for using HL-60, human leukemia cells, in place of MH-134. The results obtained are shown in Table 4.

TABLE 2

| Incubation Time (hr) | Lipid Uptake by Tumor Cells, MH-134 (nmol/4 × 10⁶ cells), n = 3 | | |
|---|---|---|---|
| | Comparative Example 2 | Example 7 | Example 8 |
| 1 | 1.03 ± 0.25 | 2.09 ± 0.21 | 3.53 ± 0.46 |
| 3.5 | 1.00 ± 0.11 | 2.81 ± 0.30 | 4.00 ± 0.20 |

(mean ± standard deviation)

TABLE 3

| Incubation Time (hr) | Lipid Uptake by Tumor Cells, MH-134 with Fetal Bovine Serum (nmol/4 × 10⁶ cells), n = 3 | | |
|---|---|---|---|
| | Comparative Example 2 | Example 7 | Example 8 |
| 1 | 0.62 ± 0.09 | 1.30 ± 0.41 | 1.41 ± 0.20 |
| 3.5 | 0.73 ± 0.17 | 1.30 ± 0.02 | 2.05 ± 0.21 |

(mean ± standard deviation)

TABLE 4

| Incubation Time (hr) | Comparative Example 2 | Lipid Uptake by Tumor Cells. HL-60 (nmol/4 × 10⁶ cells). n = 3 | |
| --- | --- | --- | --- |
| | | Example 7 | Example 8 |
| 1 | 0.74 ± 0.11 | 1.33 ± 0.22 | 1.13 ± 0.25 |
| 3.5 | 0.70 ± 0.08 | 1.34 ± 0.22 | 1.44 ± 0.09 |

(mean ± standard deviation)

As is apparent from Tables 2 to 4, the liposomes of the present invention were excellent in uptake by tumor cells comparing to Comparative Example 2.

Therefore, it was confirmed that the lipid membrane structures of the present invention have a specific affinity to the tumor cells and can be delivered preferentially to the tumor cells.

TEST EXAMPLE 3

The liposomal dispersion prepared in Example 9 was added to 2 ml of suspension culture of MH-134 cells in RPMI-1640 medium (cell number: $1.6 \times 10^6/2$ ml) in 0.16 μmol of the total lipid content. As a control, the PBS solution of 2.62 nmol insulin containing 0.157 μCi of $^3$H-inulin was added to 2 ml of another suspension culture of MH-134 cells. The mixture was incubated in a similar manner to that in Test Example 2 and the sampling was carried out at 0.5, 1, 2 and 3 hours. The uptake of inulin by tumor cells was determined in a similar manner to that in Test Example 2. The numbers of cells after the incubation were corrected by quantitative determination of protein by Lowry's method. The results obtained were shown in Table 5.

TABLE 5

| Incubation Time (hr) | Inulin Uptake by Tumor Cells, MH-134 (%/1.6 × 10⁶ cells). n = 3 | |
| --- | --- | --- |
| | Example 9 | Control (Inulin only) |
| 0.5 | 3.02 | 0.49 |
| 1 | 3.93 | 0.66 |
| 2 | 3.95 | 0.75 |
| 3 | 4.35 | 0.59 |

As is apparent from Table 5, the liposomes according to the present invention were taken up by the tumor cells, and further inulin encapsulated into the liposomes was also taken up by the tumor cells at the same time.

While the invention has been described in detail and with reference to specific embodiments thereof, it will be apparent to one skilled in the art that various changes and modifications can be made therein without departing from the spirit and scope thereof.

What is claimed is:

1. A lipid membrane structure comprising, in a lipid membrane or salt thereof, a compound represented by formula (I):

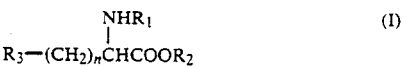

wherein
   (a) $R_1$ represents a hydrogen atom or a fatty acid residue, said fatty acid residue having 1 to 30 carbon atoms;
   (b) $R_2$ represents a hydrogen atom or acyclic hydrocarbon residue, said acyclic hydrocarbon residue having 1 to 30 carbon atoms;
   (c) $R_3$ represents an amino group, a guanidino group or an amidino group;
   (d) n represents an integer of from 1 to 6, provided that $R_1$ and $R_2$ do not both represent a hydrogen atom; and
   (e) a sum of a number of carbon atoms of said fatty acid residue and said acyclic hydrocarbon residue is n the range of from 10 to 40 carbon atoms.

2. A lipid membrane structure as claimed in claim 1, wherein the fatty acid residue contains from 14 to 20 carbon atoms.

3. A lipid membrane structure as claimed in claim 1, wherein the acyclic hydrocarbon residue contains from 14 to 20 carbon atoms.

4. A lipid membrane structure as claimed in claim 1, wherein n is 3 or 4.

5. A lipid membrane structure as claimed in claim 1, wherein said lipid membrane structure is selected from the group consisting of a liposome, a micelle and a microemulsion.

6. A lipid membrane structure as claimed in claim 1, wherein a molar ratio of said compound of formula (I) or a sat thereof to the total content of the lipid components is at least about 1/40.

* * * * *